US010180479B2

(12) United States Patent
Meriles et al.

(10) Patent No.: US 10,180,479 B2
(45) Date of Patent: Jan. 15, 2019

(54) METHOD FOR INDUCING SPIN POLARIZATION IN AN ANALYTE USING $^{14}N$ SPIN DEFECT CENTERS

(71) Applicant: Research Foundation of the City University of New York, New York, NY (US)

(72) Inventors: Carlos A. Meriles, Fort Lee, NJ (US); Daniela Pagliero, Fort Lee, NJ (US); Abdelghani Laraoui, Bronx, NY (US)

(73) Assignee: Research Foundation of the City University of New York, New York, NY (US)

( * ) Notice: Subject to any disclaimer, the term of this patent is extended or adjusted under 35 U.S.C. 154(b) by 351 days.

(21) Appl. No.: 14/961,974

(22) Filed: Dec. 8, 2015

(65) Prior Publication Data
US 2016/0161583 A1    Jun. 9, 2016

Related U.S. Application Data

(60) Provisional application No. 62/088,949, filed on Dec. 8, 2014.

(51) Int. Cl.
*G01V 3/00* (2006.01)
*G01R 33/56* (2006.01)
(Continued)

(52) U.S. Cl.
CPC ......... *G01R 33/5605* (2013.01); *G01N 24/08* (2013.01); *G01R 33/282* (2013.01)

(58) Field of Classification Search
CPC .. G01R 33/032; G01R 33/60; G01R 33/1284; G01R 33/24; G01R 33/282;
(Continued)

(56) References Cited

U.S. PATENT DOCUMENTS

2010/0308813 A1* 12/2010 Lukin ................. G01R 33/032
324/244.1
2016/0054402 A1*  2/2016 Meriles ............... G01R 33/282
324/309

FOREIGN PATENT DOCUMENTS

WO    WO2014165845    10/2014
WO    2016188557      12/2016

OTHER PUBLICATIONS

Abrams, Daniel et al.; Dynamic Nuclear Spin Polarization of Liquids and Gases in Contact with Nanostructured Diamond; Nanoletters; Apr. 22, 2014; pp. 2471-2478; American Chemical Society; US.

(Continued)

*Primary Examiner* — Vinh Nguyen
(74) *Attorney, Agent, or Firm* — Peter J. Mikesell; Schmeiser, Olsen & Watts, LLP

(57) ABSTRACT

A method of inducing spin polarization in an analyte is provided. The method exposes $^{14}N$ spin defect centers embedded within 25 nm of a diamond surface to a magnetic field while an analyte is near the surface. The $^{14}N$ spin defect centers are polarized by treatment with an electromagnetic wave protocol having a visible light pulse (p0); a microwave pulse (mw1), a radio frequency pulse (rf1), a microwave pulse (mw2) and a radio frequency pulse (rf2) resulting in polarization of the nuclear spins of the $^{14}N$ spin defect centers. Polarized spins in the $^{14}N$ spin defect centers induce spin polarization in the analyte.

14 Claims, 9 Drawing Sheets

(51) Int. Cl.
*G01N 24/08* (2006.01)
*G01R 33/28* (2006.01)

(58) Field of Classification Search
CPC .............. G01R 33/302; G01R 33/323; G01R 33/5605; G01R 29/0885; G01R 33/26; G01R 33/307; G01R 33/62; G01N 33/54326; G01N 33/585; G01N 33/587; G01N 24/08; G01N 21/66; H01L 2924/00014; G01B 15/00; G01V 3/14; H01S 3/0326; H01S 3/0602; H01S 3/10007; H01S 4/00
See application file for complete search history.

(56) References Cited

OTHER PUBLICATIONS

Belthangady, C. et al.; Dressed-State Resonant Coupling between Bright and Dark Spins in Diamond; Physical Review Letters; Apr. 12, 2013; pp. 1-5; vol. 110, Issue 15; American Physical Society; US.

Fischer Ran et al.; Bulk Nuclear Polarization Enhanced at Room Temperature by Optical Pumping; Physical Review Letters; Aug. 2, 2013; pp. 1-5; vol. 111, Issue 5; American Physical Society; US.

Jacques, V. et al; Dynamic Polarization of Single Nuclear Spins by Optical Pumping of Nitrogen-Vacancy Color Centers in Diamond at room Temperature; Feb. 6, 2009; pp. 1-4; vol. 102, Issue 5; American Physical Society; US.

Jiang, L. et al; Repetitive Readout of a Single Electronic Spin via Quantum Logic with Nuclear Spin Ancillae; Science; Oct. 9, 2009; pp. 267-272; vol. 326; Science; US.

Laraoui, Abdelghani et al.; Approach to Dark Spin Cooling in a Diamond Nanocrystal; Acsnano; Apr. 8, 2013; pp. 3403-3410; vol. 7, No. 4; American Chemical Society; US.

Laraoui, Abdelghani et al.; Rotating frame spin dynamics of a nitrogen-vacancy center in a diamond nanocrystal; Physical Review; Oct. 10, 2011; pp. 161403-1-161403-4; vol. 84, Issue 16; Physical Review US.

London, P. et al.; Detecting and Polarizing Nuclear Spins with Double Resonance on a Single Electron Spin; Physical Review Letters; Aug. 5, 2013; pp. 067601-1-067601-5; vol. 111, Issue 6; American Physical Society; US.

Neumann, Philipp et al.; Single-Shot Readout of a Single Nuclear Spin; Science; Jul. 30, 2010; pp. 542-544; vol. 329, No. 5991; Science; US.

Pagliero, Daniela et al.; Recursive polarization of nuclear spins in diamond at arbitrary magnetic fields; Applied Physics Letters; Dec. 15, 2014; pp. 242402-2-242402-5; vol. 105, AIP Publishing LLC; US.

Wang, Hai-Jing et al.; Sensitive magnetic control of ensemble nuclear spin hyperpolarization in diamond; Nature communications; Jun. 5, 2013; pp. 1-7; Article No. 1940; Macmillan Publishers Limited.; US.

Osterfeld, S. et al.; Multiplex protein assays based on real-time magnetic nanotag sensing; PNAS; Dec. 30, 2008; pp. 20637-20640; vol. 105, No. 52.

Madou, M. et al.; Chemical Sensing with Solid State Devices; Academic Press, Inc.; 1989; 39 pages.

Janata, J. et al.; Solid State Chemical Sensors; Academic Press, Inc.; 1985; 26 pages.

\* cited by examiner

METHOD FOR INDUCING SPIN POLARIZATION IN AN ANALYTE USING $^{14}$N SPIN DEFECT CENTERS

CROSS-REFERENCE TO RELATED APPLICATIONS

This application claims priority to and is a non-provisional of U.S. Patent Application Ser. No. 62/088,949 (filed Dec. 8, 2014) the entirety of which is incorporated herein by reference.

STATEMENT OF FEDERALLY SPONSORED RESEARCH OR DEVELOPMENT

This invention was made with Government support under Contract numbers NSF-1401632, NSF-1309640 and NSF-1314205 awarded by the National Science Foundation. The government has certain rights in the invention.

BACKGROUND OF THE INVENTION

The subject matter disclosed herein relates to magnetic resonance including nuclear magnetic resonance and electron magnetic resonance. Spin polarization is important to magnetic resonance and thus to analytical science. Some strategies of 'dynamic' polarization of nuclear spins have been introduced in the past. However, they either work at very low temperatures (10K and below) or are incapable of generating polarization superior to that obtained with the use of a strong magnet. Despite these limitations, higher spin polarization is in such high demand that several companies have developed complex (and very expensive) instruments that partly overcome these problems. Here the sample is previously cooled down to about 10K or below, hyperpolarized, thawed and then quickly transferred to the high-field magnet in the form of a polarized fluid. Such systems are not only pricy but also expensive to operate. Most existing technologies for nuclear spin polarization enhancement belong to one of the categories identified below.

Dynamic Nuclear Polarization Via the Overhauser Effect:

In this case a radical (i.e., a molecule containing unpaired electron spins) is dissolved in the target fluid. A continuous radio-frequency (or microwave) field is applied at the electronic Zeeman frequency of the radical. The enhancement is proportional to the thermal polarization of the unperturbed nuclear system (i.e., grows with the applied magnetic field) and reaches up to 600 times (in practice, the enhancement typically reaches less than 200 times). Because the technique only works at relatively low fields (up to 0.1-0.3 T), similar polarization can be attained by simply immersing the sample in a superconducting NMR magnet (10 to 20 T).

Optical Pumping of Semiconductors:

This technique uses laser light to generate polarized photoelectrons, which can then transfer the polarization to nuclei upon recombination. This technique exploits very specific optical selection rules found in semiconductors. It has been shown that this polarization can, in principle, be transferred to solid organic films deposited on top of the semiconductor material. Unfortunately, the technique exclusively works at very low temperatures (below 10K) and thus finds reduced applicability.

Contact with Hyperpolarized Xenon (or Other Noble Gases):

In this case, xenon gas is first polarized by contact with optically pumped Rubidium vapor (or some other alkaline vapor). To produce pure hyperpolarized Xenon gas, Rubidium (as well as other atoms such as nitrogen) are removed from the gas mixture by a freeze-thaw cycle. Pure Xenon gas is then dissolved in the liquid sample of interest (or blown on the solid surface to be studied). Polarization is then transferred via a process known as SPINOE. While high levels of Xenon polarization can be attained, the ultimate nuclear polarization of the target fluid is somewhat small because xenon does not dissolve well enough. Also, the generation of hyperpolarized Xenon is far from trivial, requiring optical excitation, applied magnetic fields, relatively high temperatures (about 450 K), a controlled gas mixture, the removal of Rubidium (which is toxic), etc.

International Patent publication WO2014/165845 uses green light to continuously illuminate nitrogen vacancy (NV) centers and spin relaxation leads to nuclear spin polarization on a diamond surface. The technique disclosed in an article entitled "Recursive Polarization of Nuclear Spins in Diamond at Arbitrary Magnetic Fields" in Applied Physics Letters 105 (Dec. 15, 2014) 242402 demonstrates nitrogen polarization of about 80% at room temperature (e.g. 25° C.±5° C.) and in the presence of only a very small magnetic field. This corresponds to approximately six orders of magnitude higher polarization than that possible with the strongest NMR magnet commercially available today. While the prior technique is useful in some situations, a more general and versatile version of this approach is desirable. The content of WO2014/165845 is hereby incorporated by reference.

The discussion above is merely provided for general background information and is not intended to be used as an aid in determining the scope of the claimed subject matter.

BRIEF DESCRIPTION OF THE INVENTION

A method of dynamically polarizing the nuclear spin host of nitrogen-vacancy (NV) centers in diamond is provided. The method uses optical, microwave and radio-frequency pulses to recursively transfer spin polarization from the NV electronic spin. Nitrogen nuclear spin initialization approaching 80% at room temperature is demonstrated both in ensemble and single NV centers without relying on level anti-crossings. An advantage that may be realized in the practice of some disclosed embodiments of the method is that the method is applicable at arbitrary magnetic fields.

In a first embodiment, a method for polarizing spins is provided. The method comprises steps of exposing a substrate to a magnetic field, the substrate comprising a surface with a plurality of $^{14}$N spin defect centers within 25 nm of the surface; treating the plurality of $^{14}$N spin defect centers with electromagnetic waves according to a protocol to produce polarized spins in the $^{14}$N spin defect centers, wherein the protocol comprises sequential pulses of: a first visible light pulse (p0); a first microwave pulse (mw1); a first radio frequency pulse (rf1); a second microwave pulse (mw2); a second radio frequency pulse (rf2).

In a second embodiment, a method for polarizing spins is provided. The method comprises steps of exposing a substrate to a magnetic field, the substrate comprising a surface with a plurality of $^{14}$N spin defect centers within 25 nm of the surface; treating the plurality of $^{14}$N spin defect centers with electromagnetic waves according to a protocol to produce polarized spins in the $^{14}$N spin defect centers, wherein the protocol comprises sequential pulses of: a first visible light pulse (p0) with a wavelength between 500 nm and 637 nm; a first microwave pulse (mw1) with a first microwave frequency between 10 MHz and 300 GHz; a first radio frequency pulse (rf1) with a first radio frequency between 10 kHz and 100 MHz; a second microwave pulse (mw2) with a second microwave frequency between 10 MHz and 300 GHz; a second radio frequency pulse (rf2) with a second radio frequency between 10 kHz and 100 MHz.

In a third embodiment, method for polarizing spins is provided. The method comprises steps of introducing an analyte to a surface of a substrate comprising a plurality of $^{14}N$ spin defect centers implanted within 25 nm of the surface; exposing the spin in defect centers to a magnetic field while the analyte is proximate the surface; treating the plurality of $^{14}N$ spin defect centers with electromagnetic waves according to a protocol to produce polarized spins in the spin defect centers, wherein the protocol comprises sequential pulses of: a first visible light pulse (p0); a first microwave pulse (mw1); a first radio frequency pulse (rf1); a second microwave pulse (mw2); a second radio frequency pulse (rf2); permitting the polarized spins in the $^{14}N$ spin defect centers to induce spin polarization in the analyte.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE INVENTION

Figure 1A:
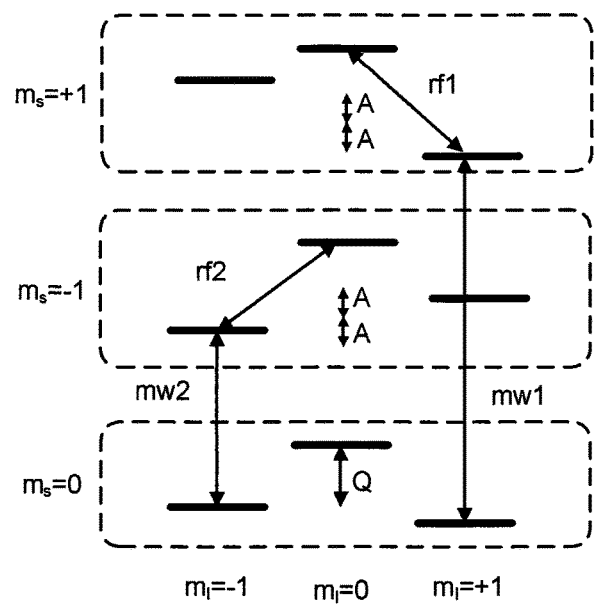
FIG. 1A is an energy level diagram of the NV-$^{14}N$ system in the NV ground state; Q and A respectively denote the amplitudes of the nitrogen quadrupolar and hyperfine couplings.

Disclosed in this specification is a method of dynamically polarizing the nuclear spin host of nitrogen-vacancy (NV) centers in diamond. The disclosed method uses optical, microwave and radio-frequency pulses to recursively transfer spin polarization from the NV electronic spin. Using two complementary variants of the same underlying principle, nitrogen nuclear spin initialization approaching 80% at room temperature is demonstrated in both ensemble and single NV centers. Unlike existing schemes, the disclosed method does not rely on level anti-crossings and is thus applicable at arbitrary magnetic fields. This versatility is useful in applications ranging from nanoscale metrology to sensitivity-enhanced NMR.

Formed by a nitrogen impurity adjacent to a vacant site, the nitrogen-vacancy (NV) center in diamond is emerging as a promising platform for multiple applications in photonics, quantum information science, and nanoscale sensing. A fortuitous combination of electronic structure, intersystem crossing rates, and selection rules allows the NV ground state spin-triplet (S=1) to completely convert into the $m_s=0$ magnetic sublevel upon optical illumination. This easily obtainable pure quantum state provides the basis to initialize the NV spin and, perhaps more importantly, other neighboring spins that cannot be polarized by optical means. For example, the nuclear spin of the nitrogen host polarizes almost completely near 50 mT, where the NV experiences a level anti-crossing (LAC) in the excited state. Further, nuclear spin hyperpolarization has been observed in strongly coupled carbon spins at 50 mT and 100 mT, mediated by NV LACs in the excited and ground states, respectively. Alternatively, efficient polarization transfer from the NV was demonstrated via the use of Hartman-Hahn (HH) protocols adapted to the doubly rotating frame—to polarize other paramagnetic species—or to the mixed rotating/lab frame—to selectively polarize adjacent carbons.

This disclosure provides a method that simultaneously exploits the singular energy level structure of an NV-$^{14}$N pair in the ground state as well as the robustness of the nuclear spin state against optical excitation of the NV. Two complementary schemes are described. The first scheme, referred to as "spin exchange," concatenates optical excitation with selective microwave (mw) and radio-frequency (rf) pulses to exchange the initial NV and nitrogen spin states. The second scheme, referred to as "population trapping," uses a similar pulse sequence to sequentially drag the NV-$^{14}$N system into a target polarized state. Interestingly, this class of schemes promises some advantages when compared to LAC-based and HH-based methods, particularly when nuclear polarization at high magnetic field is desired.

The experiments herein are carried out using a confocal microscope adapted for optically-detected magnetic resonance, as described previously (see Laraoui et al., Phys. Rev. B 84, 161403 (2011)). Briefly, the NV (nitrogen) spin is manipulated via the mw (rf) field created by a copper wire stretching the diamond surface. Short pulses (less than 1 μs) of green laser light (532 nm) are applied to either polarize or readout the NV spin state (the NV fluorescence is brighter in the $m_s=0$ state of the ground state triplet. In one embodiment, the pulse has a wavelength between 500 nm and 637 nm. Both single-NV and ensemble measurements were conducted using two {111} diamond crystals (type IIa and Ib, respectively) with typical NV spin coherence lifetimes of about 300 μs.

To more clearly describe the method to transfer polarization one may begin by considering the energy level structure of an NV-spin pair (FIG. 1A). In the ground state, the NV exhibits a spin triplet with zero field splitting $\Delta \sim 2.87$ GHz. Each of these levels, however, unfolds into three different states depending on the energy of the $^{14}$N nuclear spin (itself a spin I=1 system subject to a quadrupolar coupling Q about 5 MHz). The NV-$^{14}$N hyperfine coupling of magnitude A (about 2.2 MHz) vanishes in the $m_s=0$ state of the NV but it must be accounted for in the $m_s=\pm 1$ levels. Further, the presence of a magnetic field aligned with the NV axis breaks the degeneracy between the $m_s=\pm 1$ levels (as well as the $m_I=\pm 1$ states in the $m_s=0$ subspace) thus making it possible to distinguish all transitions of the spin pair (FIG. 1A).

Figure 1B:
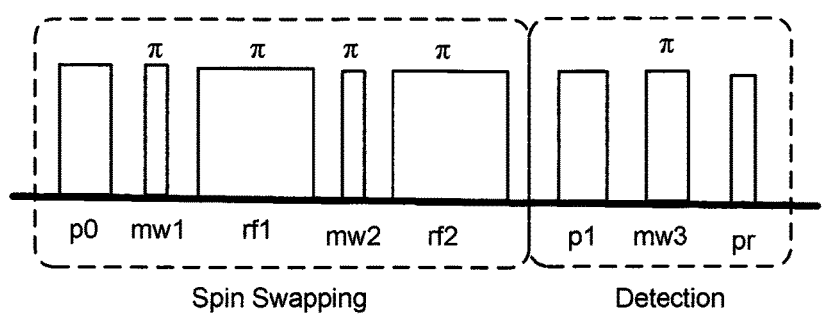
FIG. 1B is a spin exchange protocol; p0 and p1 denote light pulses, pr indicates a readout laser pulse, and mw3 is a narrowband microwave pulse of variable frequency.

The first scheme to polarization transfer rests on the one-to-one correspondence between the NV and $^{14}$N spin states. A schematic of the pulse protocol is presented in FIG. 1B. After optical initialization of the NV into $m_s=0$, a set of four consecutive mw and rf inversion pulses are applied, each of which is tailored to act selectively on a given target transition, as shown in the figure. Assuming an initial mixed state of the form $\alpha|m_s=0\ \mu m_I=1\rangle +\beta|m_s=0\ \mu m_I=0\rangle +\gamma|m_s=0\ \mu m_I=-1\rangle$, the first two pulses lead to $\alpha|m_s=1\ \mu m_I=0\rangle +\beta|m_s=0\ \mu m_I=0\rangle +\gamma|m_s=0\ \mu m_I=-1\rangle$, while the second pair produces the final target state $\alpha|m_s=1\ \mu m_I=0\rangle +\beta|m_s=0\ \mu m_I=0\rangle +\gamma|m_s=-1\ \mu m_I=0\rangle$. Therefore, the pulse sequence acts as a state exchange (SE) protocol transferring the initial spin polarization to the nitrogen and leaving the NV spin in a mixed, unpolarized state.

Figure 1C:
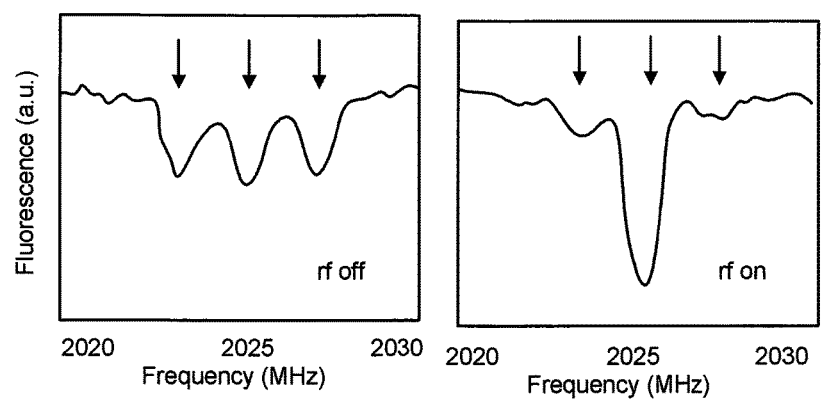
FIG. 1C depicts a NV ODMR spectrum at 30 mT $|m_s=0\rangle \leftrightarrow |m_s=-1\rangle$ transition) of a type Ib diamond (ensemble measurement); the arrows indicate the spectral positions of the $^{14}N$ hyperfine-shifted dips; the right plot shows the spectra after application of the method wherein a prominent dip in the spectrum reveals almost full initialization of the $^{14}N$ spin into $|m_I=0\rangle$; the left plot shows, in contrast, three equivalent dips (corresponding to no nuclear spin polarization) are present when the rf amplifier is turned off.

To monitor the spin transfer efficiency a pulsed ESR protocol was applied in which the NV is repolarized and its fluorescence measured immediately after the application of a narrow band inversion pulse. FIG. 1C shows the resulting hyperfine-split spectrum as the frequency of the probe pulse was scanned throughout the $|m_s=0\rangle \leftrightarrow |m_s=-1\rangle$ group of transitions. Unlike the case with no spin transfer, the dip corresponding to the transition $|m_s=0\ \mu m_I=0\rangle \leftrightarrow |m_s=-1\ \mu m_{s,I}=0\rangle$ becomes prominent, implying that the nitrogen spin has been successfully initialized into the $m_I=0$ state. More quantitatively, from the ratio between the central peak and satellite amplitudes, the fractional nuclear spin population in the $m_I=0$ state is estimated to be on the order of 75%, corresponding to a sub-milli-Kelvin nuclear spin temperature.

Figure 2A:
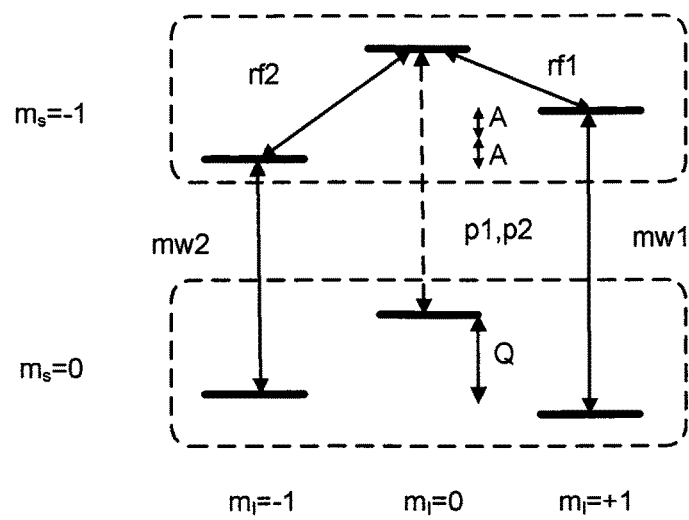
FIG. 2A is a simplified NV-$^{14}N$ energy diagram.
Figure 2B:
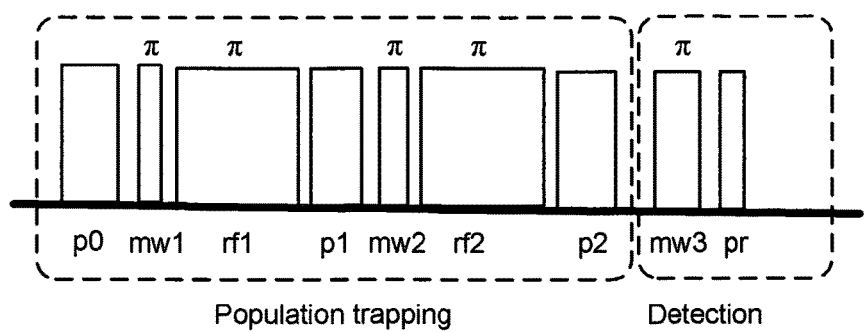
FIG. 2B is a pulse sequence comprising the population trapping and detection protocols; mw3 denotes a selective mw pulse of variable frequency and pr is a readout light pulse.

Implicit in the experiment above is the condition that the NV can be re-pumped into the $m_s=0$ state without affecting the nuclear spin state. This notion can be further exploited to implement the alternate nuclear spin pumping protocol of FIG. 2A. A total of four mw and rf pulses is used, but in this case all microwave pulses act exclusively on one of the two possible NV transitions, $|m_s=0\rangle \leftrightarrow |m_s=\pm 1\rangle$. The microwave pulses have a frequency between 10 MHz and 300 GHz. The radio frequency pulses have a frequency between 10 kHz and 100 MHz. This scheme can be understood as a "population trapping" (PT) scheme attained via consecutive CNOT gates in the form of selective π-pulses. On the condition that the initial nuclear spin quantum number is $m_I=+1$, the first pair of mw and rf pulses—here assumed to act on the $|m_s=0\rangle \leftrightarrow |m_s=-1\rangle$ set of transitions—maps the state $|m_s=0\ \mu m_I=+1\rangle$ into $|m_s=-1\ \mu m_I=0\rangle$. The latter is subsequently transformed into $|m_s=0\ \mu m_I=0\rangle$ via the application of a pump laser pulse (denoted as p1 in FIG. 2B). Similarly, if the initial nuclear spin state is $m_I=-1$, the second train of mw, rf, and light pulses maps the state $|m_s=0\ \mu m_I=-1\rangle$ into $|m_s=0\ \mu m_I=0\rangle$ which consequently becomes the only possible final state of the spin pair.

Figure 2C:
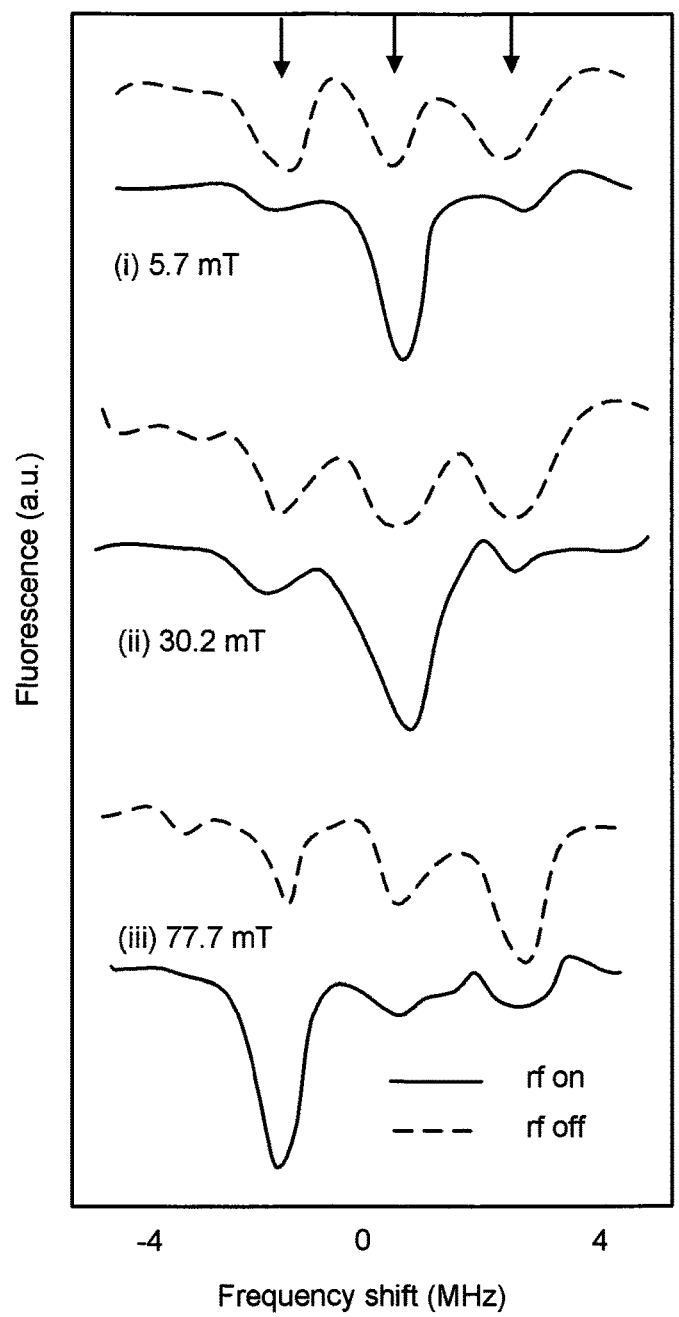
FIG. 2C depicts a NV ODMR spectra after application of the sequence in (FIG. 2B) at 5.7 mT (top), 30.2 mT (middle) and 77.7 mT (bottom) referred to as cases (i), (ii) and (iii), respectively, wherein cases (i) and (iii) correspond to single NV measurements in a type IIa diamond crystal whereas case (ii) corresponds to NV ensemble measurements in a type Ib crystal; in case (iii), the pulse protocol in FIG. 2A was modified so that mw2 acts selectively on the $|m_s=0\ \mu m_I=0\rangle \leftrightarrow |m_s=-1\ \mu m_I=0\rangle$ transition.

FIG. 2C shows the hyperfine-split spectra corresponding to the NV $|m_s=0\rangle \leftrightarrow |m_s=-1\rangle$ transition after applying the PT protocol at three different magnetic fields. Similar to FIG. 1C, nitrogen initialization ranging from 75 to 80 percent is obtained, depending on the applied magnetic field. From among the three cases disclosed, the highest pumping efficiency is attained at 5 mT, where level mixing between the electronic and nuclear spin states in the optically excited NV triplet is comparatively lower (see below). Similar initialization efficiency is attained in single NVs (cases (i) and (iii)) and NV ensembles (case (ii)) indicating that this protocol can be used to generate bulk nuclear spin polarization. Naturally, the pulse sequence can be altered to polarize a different target nuclear spin state. This is shown in case (iii) where the second microwave pulse is tuned into the $|m_s=0\ \mu m_I=0\rangle \leftrightarrow |m_s=-1\ \mu m_I=0\rangle$ transition, thus trapping the nitrogen nuclear spin population into the $m_I=-1$ state. Note that efficient nitrogen initialization is attained even in the presence of partial level mixing in the NV excited triplet state (the mechanism responsible for the preferential pumping of the $^{14}$N into $m_I$=+1 observed in the absence of rf, blue traces in case (iii)).

Interestingly, the ability to repump the NV into $|m_s=0\rangle$ without (significantly) affecting the nitrogen state makes both spin transfer schemes above one-directional, meaning that they can be applied recursively so as to mitigate system imperfections (e.g., mw and/or rf inhomoneity, or frequency offsets). This notion is demonstrated in FIG. 3A and FIG. 3B where the PT sequence is repeated a variable number of times while purposely setting the duration of the rf pulses away from the ideal value. In one embodiment, the sequence is repeated at least four times within a second. In another embodiment, the sequence is repeated at least six times within a second. To probe the $^{14}$N populations in this case a Ramsey sequence was applied and subsequently the NV response was subjected to a Fourier-transform. Given the long-term memory of the nuclear magnetization and the need to average the NV signal over multiple runs of the pulse sequence, the readout pulse pr—typically 250 ns long—was prolonged over a longer time interval (10 µs). The goal is to erase at the end of each run the polarization gain attained during the spin transfer (see below) so as to reset the NV-$^{14}$N system to the same (known) initial state.

Figure 3A:
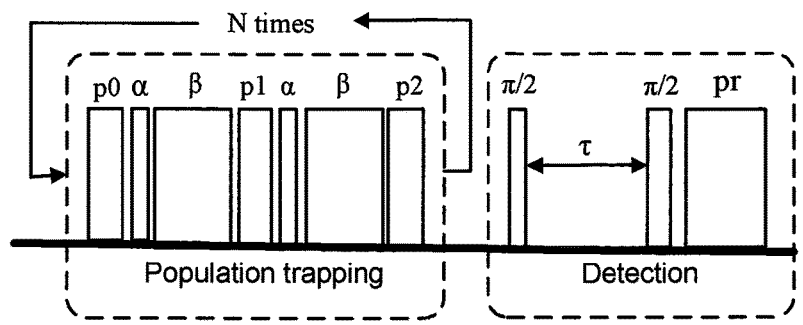
FIG. 3A illustrates a recursive application of the population trapping protocol where detection was carried out via a Ramsey sequence followed by a 10 μs light pulse so as to ensure complete nuclear spin depolarization between successive applications of the protocol.
Figure 3B:
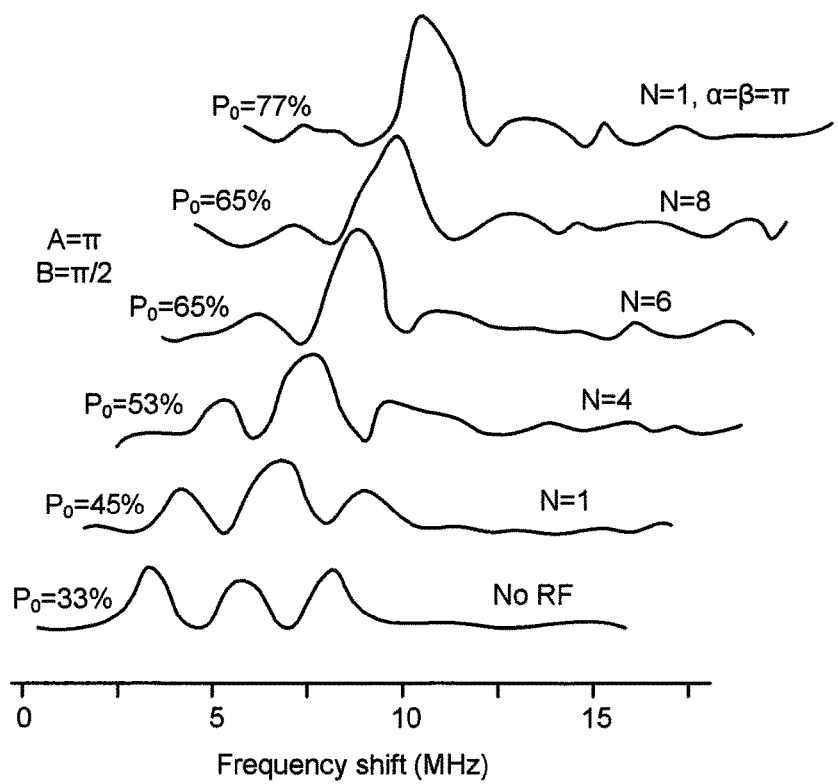
FIG. 3B depicts a NV spectra after Fourier transform of the signal in FIG. 3A wherein the rf duration of $\beta=\pi/2$ (i.e., one half the ideal value) was chosen; N indicates the number of repeats in the pumping cycle and $P_0$ denotes the estimated fractional population of the $m_I=0$ state, the spectrum corresponding to N=1 and $\alpha=\beta=\pi$ (optimum transfer) is also included for reference.

The results are shown in FIG. 3B where the observed NV spectra is plotted for a different number n of transfer cycles. In this particular example, the rf pulses was purposely set to $\beta=\pi/2$ (i.e., half the ideal value) while keeping the mw duration near its optimum (i.e., $\alpha=\pi$). By comparing the relative amplitudes in the hyperfine-split spectra, a one-time application of the spin transfer protocol was found to produce only a mild change in the $^{14}$N populations (n=1 in FIG. 3B). As n increases, however, a progressive growth of the $m_I$=0 peak towards a maximum was observed, which remains unchanged when n is greater than or equal to six. This maximum is slightly smaller than that attained when $\beta=\pi$ (denoted as "Optimum transfer"), a trend confirmed through additional observations using various values of $\alpha$ and $\beta$. The exact asymptotic limit—as well as the convergence rate—is found to be a function of the chosen conditions, which points to a complex interplay between the number of pumping cycles, the mw/rf offset, and the effect of laser illumination (itself a function of the pulse duration and applied magnetic field).

Figure 4A:
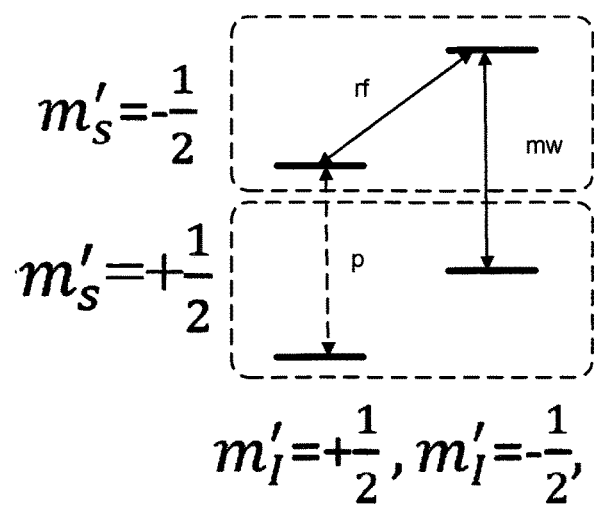
FIG. 4A illustrates a toy-model energy diagram for a virtual, hyperfine-coupled electron/nuclear spin pair, assuming preferential optical pumping into $m_s'=+\frac{1}{2}$, nuclear spin initialization into $m_I'=+\frac{1}{2}$ is attained via the application of selective mw, and light pulses, as shown.

A semi-quantitative understanding of the observed response was gained by considering the simplified model of FIG. 4A. Here a hypothetical system of coupled electron and nuclear spins—both sharing the same spin number $S'=I'=\frac{1}{2}$—undergo repeated cycles of dynamic polarization into the target state $|m_s'=+\frac{1}{2}\mu m_I'=+\frac{1}{2}\rangle$. Under the combined action of the mw and rf pulses (not necessarily performing ideally), the nuclear spin experiences a flip with probability $p_a \lesssim 1$. Similar to the NV, the light pulse is assumed to deterministically map the electron spin into the group of sublevels within $\{m_s'=+\frac{1}{2}\}$ and that this process may be accompanied by a nuclear spin flip with probability $p_b \gtrsim 0$.

Under these conditions, the relative populations in the $m_s'=+\frac{1}{2}$ subspace at the end of the n-th pumping cycle are given by $P_-^{(n)}=P_-^{(n-1)}q+p_b$ and $P_+^{(n)}=1-P_-^{(n)}$, where $q\equiv(1-p_a)(1-2p_b)$, and the $\pm$subscripts correspond to the $|m_I'=\pm\frac{1}{2}\rangle$ states. After N cycles, the probability of having a nuclear spin in the depleted state $|m_s'=+\frac{1}{2}\mu m_I'=-\frac{1}{2}\rangle$ amounts to $$P_-^{(n)}=P_-^{(0)}q^N p_b(1-q^N)/(1-q)$$ (equation 1)

where $P_-^{(0)}$ denotes the initial nuclear spin population in $|m_s'=+\frac{1}{2}\mu m_I'=-\frac{1}{2}\rangle$. Equation 1 indicates that convergence to the optimum nuclear spin polarization in a single cycle is possible when q=0 (corresponding to $p_a$=1 if $p_b$ is less than ½). Note that as N increases, $P_+^{(n)}=1-P_-^{(n)}$ asymptotically approaches the limit value $$P_+^{lim} = 1 - \frac{p_b}{p_a + 2p_b(1-p_a)} \leq 1 - p_b$$ (equation 2)

implying that complete nuclear spin initialization can be attained for an arbitrary value of $p_a$ when the probability of an optically induced flip is negligible. In the more general case where $p_b \neq 0$, the limit nuclear polarization grows with $p_a$ and reaches a maximum when $p_a$=1.

Figure 4B:
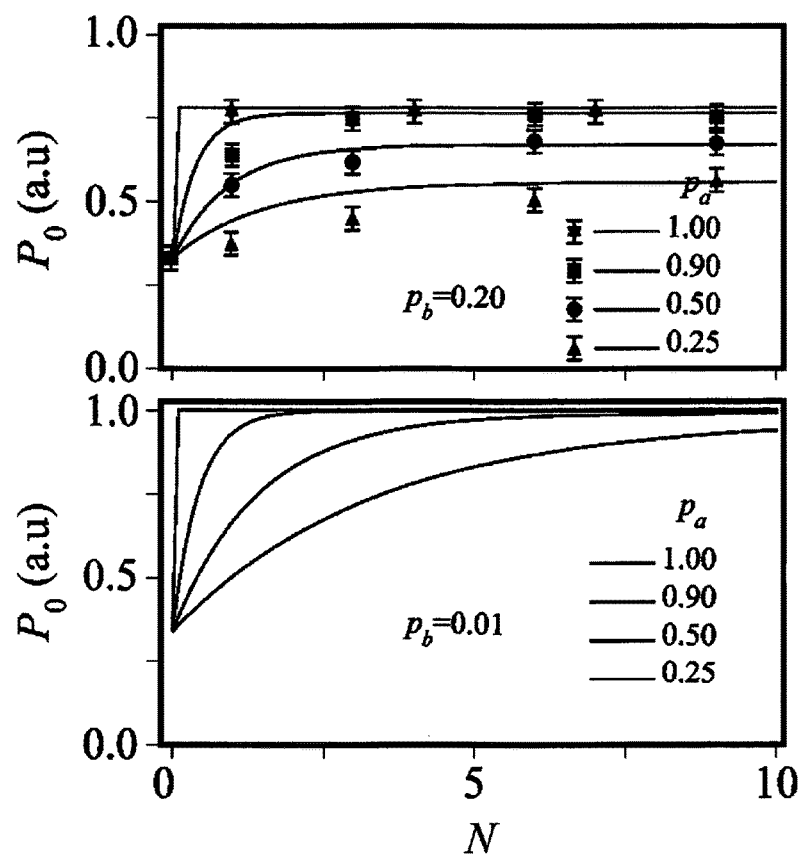
FIG. 4B depicts fractional $^{14}N$ population in the $m_I=0$—denoted as $P_0$—after N repetitions of a 'polarization trapping' (PT) protocol; in each case the duration of the if pulses is $\beta=p_a\pi$; symbols denote data points and lines correspond to the simplified model of FIG. 2B assuming an initial population $P_+^{(0)}=\frac{1}{3}$ in state $m_I'=+\frac{1}{2}$; the optical flip probability $p_b$ in the upper and lower graphs is 0.20 and 0.01, respectively.

The conclusions above are in qualitative agreement with the observations of FIG. 4B where $P_0$ is plotted—the fractional $^{14}$N population in $m_I$=0—as a function of the number of cycles N in the population trapping sequence (see FIG. 3A). A comparison between these observations and the model prediction—here included only as a reference—yields $p_b$ of about 0.20 (see top graph in FIG. 4B) for the present conditions of illumination and magnetic field. This value should be understood as a crude estimate given the more complex level structure of the NV-$^{14}$N system.

Figure 4C:
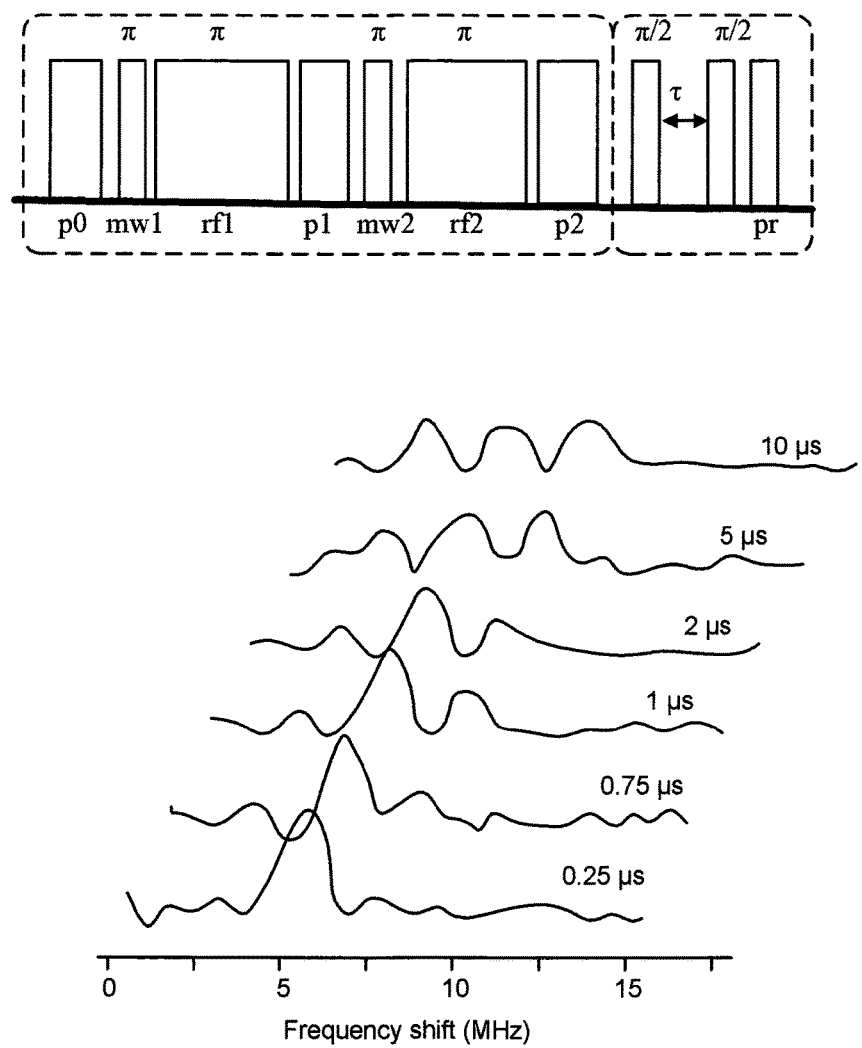
FIG. 4C illustrates a series of NV spectra for different durations of the light pulse p2; all other light pulses have a duration of 250 ns and all mw and rf pulses correspond to $\pi$-rotations.
Figure 4D:
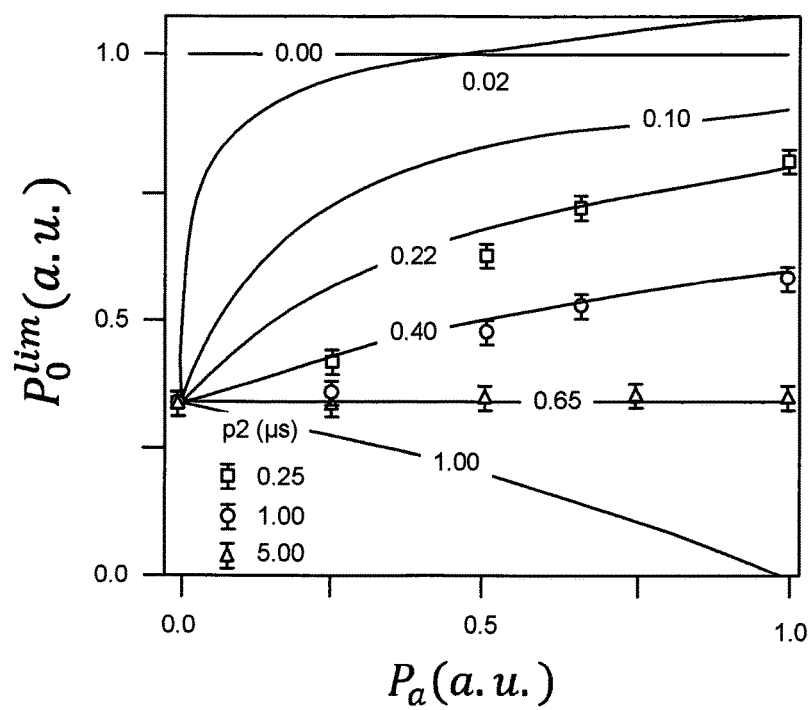
FIG. 4D depicts a graph where symbols represent the measured limit population of the $m_I=0$ state $P_+^{lim}$ as a function of the rf-induced flip probability $p_a$ for different durations of p2, wherein lines correspond to $P_+^{lim}$ as determined from the model in (FIG. 4B); labels denote the assumed values for $p_b$.

A more direct appreciation of the effect of the optical pulses on the 14N populations is provided via the experiment of FIG. 4C. Here the NV response after application of the polarization trapping sequence is measured as the duration of the light pulse p2 is increased. In this example, all mw and rf pulses are set to their ideal durations, which allows a $^{14}$N initialization of 77% for the shortest p2 time. However, the spin pumping efficacy gradually decays as p2 becomes longer to finally vanish when the illumination interval exceeds about 5 µs. Similar results are found when the rf duration is less than optimal, with an overall scaling that depends on $p_a$, as summarized in FIG. 4D. In the context of the model above, this behavior is interpreted as a progressive growth of $p_b$, which impacts the steady state nuclear spin populations according to equation 2. Since $p_b$ decreases nearly quadratically with the applied magnetic field (above about 0.12 T), the maximum duration of p2—limited in these experiments to less than 5 µs—can become much longer provided the field is sufficiently strong.

In summary, a method is provided that polarizes nuclear spin in diamond that leverages on the relative robustness of the nuclear spin against NV optical pumping. One embodiment uses a spin swap protocol to exchange the spin states of the NV and its nuclear neighbor, whereas the other iteratively drags the nuclear spin population into a final target state. Both schemes are most effective at magnetic fields removed from the ground- or excited-states NV level anti-crossings, which makes them complementary to known polarization methods relying on nuclear/electron state mixing. In particular, because nuclear spins become increasingly decoupled from the NV at fields greater than about 150 mT, these protocols promise to be useful in situations where low-field work is inconvenient or undesired. Examples are the implementation of repetitive readout schemes (when detection sensitivity is insufficient to initialize the $^{14}$N in a "single-shot") and NMR experiments relying on inductive nuclear spin detection (impractical below 200 mT). Both schemes can be applied recursively so as to circumvent limitations arising from imperfections in the mw or rf pulses, an advantageous feature when polarizing nuclear spin ensembles using macroscopic rf coils or mw resonators. The best performance is anticipated at magnetic fields comparable to or greater than about 200 mT, where the probability of a light-induced $^{14}$N flip becomes negligible.

Several methods are conceivable to extend the transfer of spin polarization to carbon nuclei, either to selectively initialize target ancilla spins or the full $^{13}$C bath. For example, since the contact coupling of the first shell carbons in the NV ground state amounts to $A_c$ about 200 MHz (two orders of magnitude larger than nitrogen), strongly coupled carbons can be readily polarized by adapting, e.g., the population trapping protocol to a spin-½ nucleus. On the other hand, ensemble carbon polarization can be attained by transferring the $^{14}$N spin order via a Hartman-Hahn protocol. Note that although direct Hartman-Hahn transfer from the NV to carbons has already been demonstrated, a two-step process involving the $^{14}$N spin may prove advantageous at high field, where matching the mw amplitude to the carbon Zeeman frequency is impractical. Along these lines, direct flip-flops between the $^{14}$N and $^{13}$C nuclei are possible near 500 mT, where the carbon Larmor frequency approximately matches the $^{14}$N quadrupolar splitting, thus allowing for spin transfer to the carbon bath (e.g. a $^{13}$C intermediary) without the need for extra rf pulses. This method could prove useful in the polarization of near-surface $^{13}$C ensembles (i.e., $^{13}$C ensembles in diamond epilayers 50 nm thick or thinner), which, in turn, may be exploited to polarize overlaid films or fluids brought into contact with a diamond crystal.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for polarizing spins, the method comprising steps of:
    contacting an analyte with a surface of a substrate comprising a plurality of $^{14}$N spin defect centers implanted within 25 nm of the surface;
    exposing the $^{14}$N spin defect centers to a magnetic field while the analyte is proximate the surface;
    treating the plurality of $^{14}$N spin defect centers with electromagnetic waves according to a protocol to produce polarized spins in the spin defect centers, wherein the protocol comprises sequential pulses of:
        a first visible light pulse (p0);
        a first microwave pulse (mw1);
        a first radio frequency pulse (rf1);
        a second microwave pulse (mw2);
        a second radio frequency pulse (rf2);
    permitting the polarized spins in the $^{14}$N spin defect centers to induce spin polarization in the analyte.

2. The method as recited in claim 1, wherein the polarized spins are induced in the analyte by first transferring the polarized spin from the $^{14}$N spin defect centers to a $^{13}$C intermediary and thereafter transferring the polarized spin from the $^{13}$C intermediary to the analyte.

3. The method as recited in claim 2, wherein the $^{13}$C intermediary is disposed within fifty nm of the surface.

4. The method as recited in claim 1, wherein the protocol is a spin swapping protocol such that the protocol consists of the first visible light pulse (p0), the first microwave pulse (mw1), the first radio frequency pulse (rf1), the second microwave pulse (mw2) and the second radio frequency pulse (rf2).

5. The method as recited in claim 1, wherein the protocol is a population trapping protocol such that the protocol further comprises:
    a second visible light pulse (p1) performed after the first radio frequency pulse (rf1) and before the second microwave pulse (mw2);
    a third visible light pulse (p2) performed after the second radio frequency pulse (rf2).

6. The method as recited in claim 5, wherein the population trapping protocol consists of the first visible light pulse (p0), the first microwave pulse (mw1), the first radio frequency pulse (rf1), the second visible light pulse (p1), the second microwave pulse (mw2), the second radio frequency pulse (rf2) and the third visible light pulse (p2).

7. The method as recited in claim 6, wherein the first visible light pulse (p0), the second visible light pulse (p1) and the third visible light pulse (p2) each have a wavelength between 500 nm and 637 nm.

8. The method as recited in claim 6, wherein the method is performed at a temperature of 25° C.±5° C.

9. The method as recited in claim 1, wherein the step of treating is repeated at least four times within one second.

10. The method as recited in claim 1, wherein the step of treating is repeated at least six times within one second.

11. The method as recited in claim 1, wherein the substrate is a diamond crystal substrate.

12. The method as recited in claim 1, wherein the first visible light pulse (p0) has a wavelength between 500 nm and 637 nm.

13. The method as recited in claim 1, wherein the first microwave pulse (mw1) and the second microwave pulse (mw2) each have a frequency between 10 MHz and 300 GHz.

14. The method as recited in claim 1, wherein the first radio frequency pulse (rf1) and the second radio frequency pulse (rf2) each have a frequency between 10 kHz and 100 MHz.

* * * * *